United States Patent
Jo et al.

(10) Patent No.: US 8,865,273 B2
(45) Date of Patent: Oct. 21, 2014

(54) PHOTOALIGNMENT COMPOUND, PHOTOALIGNMENT COMPOSITION, DISPLAY SUBSTRATE HAVING AN ALIGNMENT LAYER, AND METHOD FOR MANUFACTURING THE DISPLAY SUBSTRATE

(75) Inventors: Sung-Chan Jo, Yongin-si (KR); Weon-Eik Oii, Suwon-si (KR)

(73) Assignee: Samsung Display Co., Ltd., Yongin, Gyeonggi-Do (KR)

( * ) Notice: Subject to any disclaimer, the term of this patent is extended or adjusted under 35 U.S.C. 154(b) by 31 days.

(21) Appl. No.: 13/568,568

(22) Filed: Aug. 7, 2012

(65) Prior Publication Data

US 2012/0301628 A1 Nov. 29, 2012

Related U.S. Application Data

(62) Division of application No. 12/481,242, filed on Jun. 9, 2009, now Pat. No. 8,257,801.

(30) Foreign Application Priority Data

Dec. 8, 2008 (KR) ................... 2008-123881

(51) Int. Cl.
  *C09K 19/00* (2006.01)
  *C09K 19/56* (2006.01)
  *C07C 217/76* (2006.01)
  *G02F 1/1337* (2006.01)

(52) U.S. Cl.
  CPC ........... *C09K 19/56* (2013.01); *G02F 1/133788* (2013.01); *C07C 217/76* (2013.01); *G02F 1/133711* (2013.01)
  USPC .......... 428/1.2; 428/1.25; 428/1.26; 349/123; 349/187; 560/55; 528/170; 528/176; 528/353

(58) Field of Classification Search
  USPC ............ 428/1.2, 1.1, 1.25, 1.26; 349/56, 123, 349/187; 252/299.4; 445/24, 58; 528/353, 528/170, 176, 189; 560/55
  See application file for complete search history.

(56) References Cited

FOREIGN PATENT DOCUMENTS

JP 2007002132 A * 1/2007

Primary Examiner — Gwendolyn Blackwell
Assistant Examiner — Ruiyun Zhang

(74) *Attorney, Agent, or Firm* — F. Chau & Associates, LLC

(57) ABSTRACT

A photoalignment compound is represented by the following Chemical Formula 1,

<Chemical Formula 1>

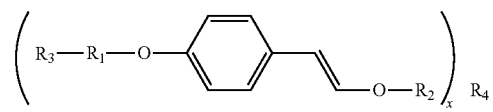

wherein "x" represents an integer in a range of 1 to 4, each of $R_1$ and $R_2$ represents —$(CH_2)_n$—, "n" represents an integer in a range of 1 to 6, at least one of the (—$CH_2$-)s in $R_1$ is replaceable with

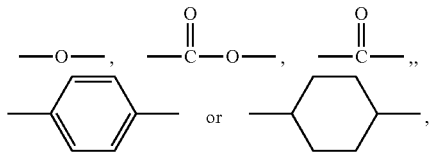

$R_3$ represents —$(CH_2)_m CH_3$, "m" represents an integer in a range of 1 to 12, each hydrogen atom of $R_3$ is replaceable with F or Cl, $R_4$ represents an amino group, aniline group, carboxy group, hydroxyl group, cyano group, alkylene group, or functional groups being represented by the following Chemical Formulas 2, 3, 4, or 5, each hydrogen atom of Chemical Formula 1 is replaceable with —$O(CH_2)_k CH_3$, —$(CH_2)_k CH_3$, F, or Cl, and "k" represents an integer in a range of 1 to 3, or 0.

<Chemical Formula 2>

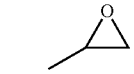

<Chemical Formula 3>

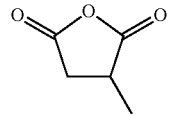

<Chemical Formula 4>

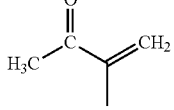

<Chemical Formula 5>

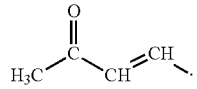

2 Claims, 5 Drawing Sheets

PHOTOALIGNMENT COMPOUND, PHOTOALIGNMENT COMPOSITION, DISPLAY SUBSTRATE HAVING AN ALIGNMENT LAYER, AND METHOD FOR MANUFACTURING THE DISPLAY SUBSTRATE

PRIORITY STATEMENT

This application is a divisional application of U.S. application Ser. No. 12/481,242 filed Jun. 9, 2009 now U.S. Pat. No. 8,257,801, which claims priority under 35 U.S.C §119 to Korean Patent Application No. 2008-123881, filed on Dec. 8, 2008, the disclosures of which are each hereby incorporated by reference herein in their entireties.

BACKGROUND OF THE INVENTION

1. Technical Field

The present disclosure relates to a photoalignment compound, a photoalignment composition, a display substrate having an alignment layer, and a method for manufacturing the display substrate. More particularly, the present disclosure relates to a photoalignment compound which is used in manufacturing an alignment layer of a liquid crystal display (LCD) device, a photoalignment composition, a display substrate having an alignment layer, and a method for manufacturing the display substrate.

2. Description of the Related Art

Generally, a liquid crystal display (LCD) panel includes a first display substrate having a thin-film transistor (TFT) as a switching element to drive a pixel, a second display substrate facing the first display substrate, and a liquid crystal layer interposed between the first display substrate and the second display substrate. An image may be displayed on the LCD panel according to the light transmittance of liquid crystal material, which may change according to voltages.

An alignment layer is formed on inner portions of each of the first display substrate and the second display substrate because it may be difficult to obtain an ideal liquid crystal molecular arrangement by only disposing the liquid crystal material between the first display substrate and the second display substrate. The alignment layer may be formed by, for example, spreading a raw alignment material using a printing roller of an alignment layer printing apparatus on a base substrate and a rubbing process. For example, the raw alignment material may be a solution including a polyimide polymer.

However, static electricity may be generated by rubbing with a rubbing cloth during the rubbing process to form the alignment layer, and thus the first or second display substrates may be damaged by the static electricity. In addition, the first or second display substrates may be readily polluted and stained in the rubbing process, thereby decreasing display quality.

To prevent static electricity and improve display quality, a photoalignment process has been developed. For example, methods including spreading a photoalignment material on the base substrate followed by photodegrading, photoisomerizing, or photopolymerizing the photoalignment material using light have been developed. The reliability of the alignment layer using the photoalignment process may depend on, for example, thermal stability, optical stability, chemical stability, alignment stability, etc. Particularly, the alignment stability of the photoalignment material may be significant for aligning the liquid crystal molecules, which is a beneficial role of the alignment layer.

However, there is still a need in the art for a photoalignment compound capable of improving the reliability of manufacturing an alignment layer and the alignment stability of the liquid crystal molecule, a photoalignment composition, a display substrate having an alignment layer, and a method for manufacturing the display substrate. In addition, there is also a need in the art for a photoalignment compound in which the developments costs are decreased.

SUMMARY OF THE INVENTION

Exemplary embodiments of the present invention may provide a photoalignment compound capable of improving the reliability of manufacturing an alignment layer and the alignment stability of the liquid crystal molecule, a photoalignment composition, a display substrate having an alignment layer, and a method for manufacturing the display substrate.

In accordance with an exemplary embodiment of the present invention, a photoalignment compound is represented by the following Chemical Formula 1 is provided.

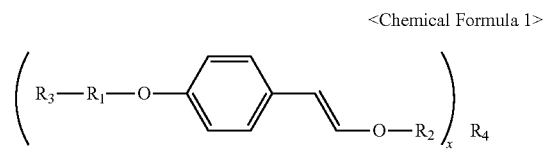

<Chemical Formula 1>

In Chemical Formula 1, "x" represents an integer in a range of 1 to 4, each of $R_1$ and $R_2$ represents —$(CH_2)_n$—, wherein "n" represents an integer in a range of 1 to 6, at least one of the (—$CH_2$-)s in $R_1$ is replaceable with

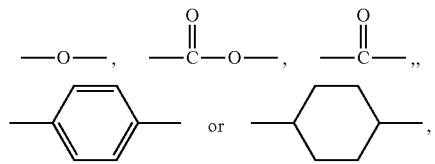

$R_3$ represents —$(CH_2)_m CH_3$, "m" represents an integer in a range of 1 to 12, each hydrogen atom of $R_3$ is replaceable with F or Cl, $R_4$ represents an amino group, aniline group, carboxy group, hydroxyl group, cyano group, alkyl group, or functional groups being represented by the following Chemical Formulas 2, 3, 4, or 5, each hydrogen atom of Chemical Formula 1 is replaceable with —$O(CH_2)_k CH_3$, —$(CH_2)_k CH_3$, F, or Cl, and "k" represents an integer in a range of 1 to 3, or 0.

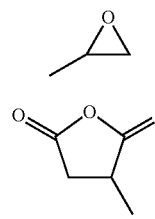

<Chemical Formula 2>

<Chemical Formula 3>

-continued

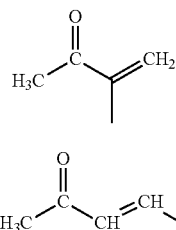
<Chemical Formula 4>

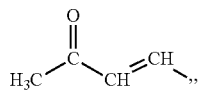
<Chemical Formula 5>

In accordance with an exemplary embodiment of the present invention, a photoalignment composition which includes a first alignment polymer and an organic solvent is provided. The first alignment polymer is a compound in which at least one hydrogen atom of a chain is replaced with a photosensitive portion represented by the following Chemical Formula 7.

<Chemical Formula 7>

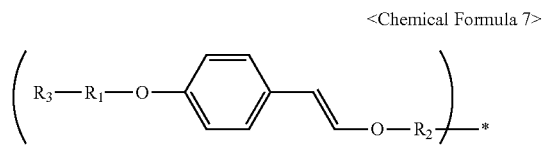

In Chemical Formula 7, each of $R_1$ and $R_2$ represents —$(CH_2)_n$—, "n" represents an integer in a range of 1 to 6, at least one of the (—$CH_2$-)s in $R_1$ is replaceable with

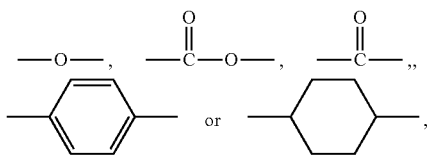

$R_3$ represents —$(CH_2)_m CH_3$, "m" represents an integer in a range of 1 to 12, and each hydrogen atom of $R_3$ is replaceable with F or Cl. The first alignment polymer includes at least one of a polyimide compound, polyamic acid compound, polyamide compound, polynorbornene compound, polyvinyl compound, polyolefin compound, polystyrene compound, polyacrylate compound, polyether compound, polyester compound, polythioether compound, polysulfone compound, polyethersulfone compound, polyetherketone compound, polyurea compound, polyurethane compound, polybenzimidazole compound, polyacetal compound, polyvinyl acetate compound, polymaleimide compound, polyphenylene phthalamide compound, azo side-chain polymer compound, polycinnamoyl compound, polychalcone compound, polycoumarin compound, etc. These may be used alone or in a combination thereof.

In an embodiment, the photoalignment composition may further include a second alignment polymer. The second alignment polymer may include at least one of a polyimide compound, polyamic acid compound, polyamide compound, polynorbornene compound, polyvinyl compound, polyolefin compound, polystyrene compound, polyacrylate compound, polyether compound, polyester compound, polythioether compound, polysulfone compound, polyethersulfone compound, polyetherketone compound, polyurea compound, polyurethane compound, polybenzimidazole compound, polyacetal compound, polyvinyl acetate compound, polymaleimide compound, polyphenylene phthalamide compound, azo side-chain polymer compound, polycinnamoyl compound, polychalcone compound, polycoumarin compound, etc. These may be used alone or in a combination thereof.

In accordance with an exemplary embodiment of the present invention, a display substrate including a base substrate, a pixel layer, and an alignment layer is provided. The pixel layer is formed on the base substrate and includes a plurality of pixel units. The alignment layer is formed on the pixel layer and includes a photoalignment polymer. The photoalignment polymer is a compound in which at least one hydrogen atom of a conventional alignment polymer is replaced with a first alignment portion represented by the following Chemical Formula 8 and/or a second alignment portion represented by the following Chemical Formula 9. The alignment polymer may include at least one of a polyimide compound, polyamic acid compound, polyamide compound, polynorbornene compound, polyvinyl compound, polyolefin compound, polystyrene compound, polyacrylate compound, polyether compound, polyester compound, polythioether compound, polysulfone compound, polyethersulfone compound, polyetherketone compound, polyurea compound, polyurethane compound, polybenzimidazole compound, polyacetal compound, polyvinyl acetate compound, polymaleimide compound, polyphenylene phthalamide compound, azo side-chain polymer compound, polycinnamoyl compound, polychalcone compound, polycoumarin compound, etc. These may be used alone or in a combination thereof.

<Chemical Formula 8>

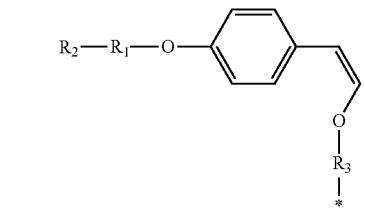

<Chemical Formula 9>

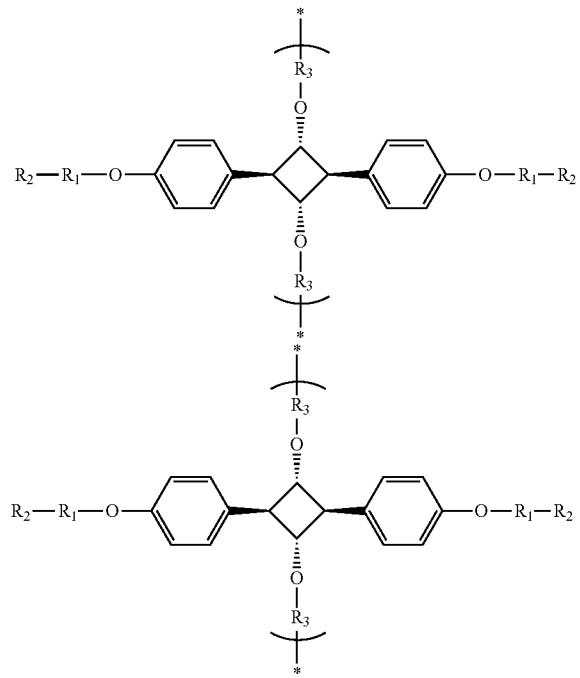

In Chemical Formulas 8 and 9, each of $R_1$ and $R_3$ represents —$(CH_2)n$-, "n" represents an integer in a range of 1 to 6, at least one of the (—$CH_2$-)s in $R_1$ is replaceable with

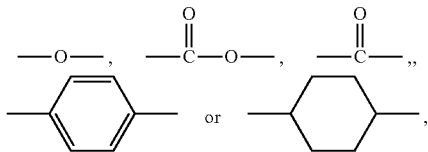

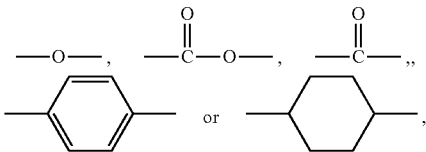

$R_2$ represents $-(CH_2)_mCH_3$, "m" represents an integer in a range of 1 to 12, and each hydrogen atom of $R_2$ is replaceable with F or Cl.

In an embodiment of the present invention, a surface of the alignment layer includes a pretilt angle.

In accordance with another exemplary embodiment of the present invention, a method for manufacturing a display substrate is provided. In the method, a pixel layer is formed on a base substrate including a plurality of pixel units, and an alignment layer is formed on the base substrate including the pixel layer. The alignment layer includes a photoalignment polymer that is a compound in which at least one hydrogen atom of a conventional alignment polymer is replaced with a first alignment portion represented by Chemical Formula 8 and/or a second alignment portion represented by Chemical Formula 9. The alignment polymer may include at least one of a polyimide compound, polyamic acid compound, polyamide compound, polynorbornene compound, polyvinyl compound, polyolefin compound, polystyrene compound, polyacrylate compound, polyether compound, polyester compound, polythioether compound, polysulfone compound, polyethersulfone compound, polyetherketone compound, polyurea compound, polyurethane compound, polybenzimidazole compound, polyacetal compound, polyvinyl acetate compound, polymaleimide compound, polyphenylene phthalamide compound, azo side-chain polymer compound, polycinnamoyl compound, polychalcone compound, polycoumarin compound, etc. These may be used alone or in a combination thereof.

<Chemical Formula 8>

<Chemical Formula 9>

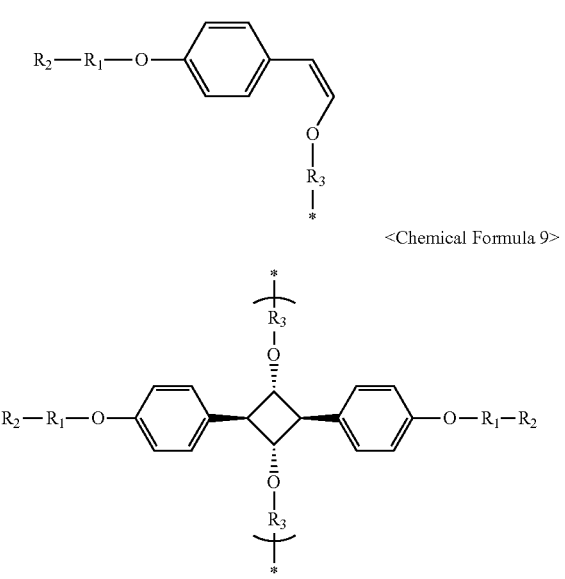

In Chemical Formulas 8 and 9, each of $R_1$ and $R_3$ represents $-(CH_2)_n-$, "n" represents an integer in a range of 1 to 6, at least one of the ($-CH_2-$)s in $R_1$ is replaceable with $R_2$ represents $-(CH_2)_mCH_3$, "m" represents an integer in a range of 1 to 12, and each hydrogen atom of $R_2$ is replaceable with F or Cl.

In an embodiment, the alignment layer may be formed by coating a photoalignment composition including a first alignment polymer on the base substrate which includes the pixel layer to form a first preliminary layer, and irradiating light to the first preliminary layer. The first alignment layer may be a compound in which at least one hydrogen atom of a conventional alignment polymer is replaced with a photosensitive portion represented by Chemical Formula 7.

In an embodiment, the first alignment polymer may be formed by a reaction between the alignment compound represented by Chemical Formula 1 and an anhydride.

In an embodiment, the alignment layer may be formed by forming a composite material layer on the pixel layer and thermally treating the base substrate including the composite material layer. The composite material layer may include a photoalignment compound represented by Chemical Formula 1 and a conventional alignment polymer.

According to the present invention, an isomerization and/or dimerization may be favored by a photosensitive portion of a photoalignment compound. A cis-type structure of the photoalignment compound may be more stable than a trans-type structure of the photoalignment compound. Thus, the manufacturing reliability of an alignment layer, the alignment reliability of the alignment layer, and alignment stability may be improved.

In addition, the photosensitive portion may be inserted into a conventional alignment material having non-photosensitivity, and thus development costs of a new photoalignment polymer may be decreased. Thus, the productivity of the product may be improved.

BRIEF DESCRIPTION OF THE DRAWINGS

Exemplary embodiments of the present invention can be understood in more detail from the following description taken in conjunction with the accompanying drawings.

DETAILED DESCRIPTION OF THE EXEMPLARY EMBODIMENTS OF THE INVENTION

Figure 1A:
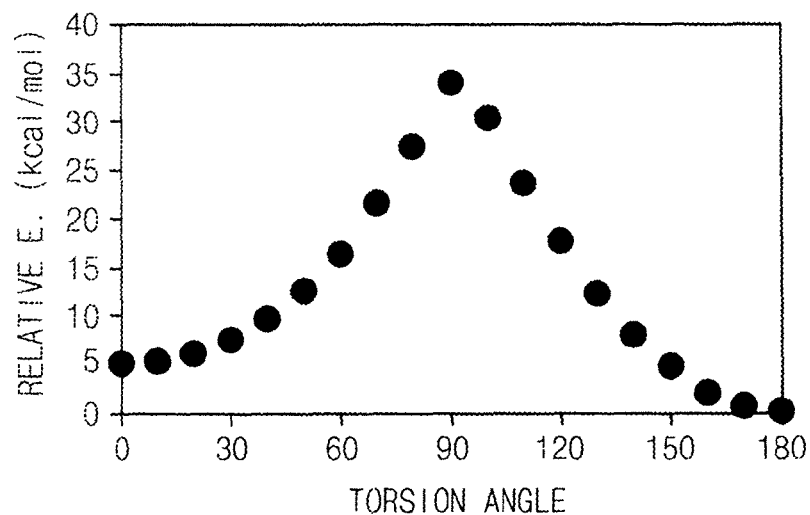
FIG. 1A is a graph illustrating relative energy according to a torsion angle of a compound according to a Comparative Example.

The present invention is described more fully hereinafter with reference to the accompanying drawings, in which example embodiments of the present invention are shown. The present invention may, however, be embodied in many different forms and should not be construed as limited to the exemplary embodiments set forth herein. In the drawings, the sizes and relative sizes of layers and regions may be exaggerated for clarity.

It will be understood that when an element or layer is referred to as being "on," "connected to" or "coupled to" another element or layer, it can be directly on, connected or coupled to the other element or layer or intervening elements or layers may be present. In contrast, when an element is referred to as being "directly on," "directly connected to" or "directly coupled to" another element or layer, there are no intervening elements or layers present. Like numerals refer to like elements throughout. As used herein, the term "and/or" includes any and all combinations of one or more of the associated listed items.

It will be understood that, although the terms first, second, third, etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention.

Spatially relative terms, such as "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

The terminology used herein is for the purpose of describing particular an embodiment only and is not intended to be limiting of the present invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Embodiments of the invention are described herein with reference to cross-sectional illustrations that are schematic illustrations of idealized embodiments (and intermediate structures) of the present invention. As such, variations from the shapes of the illustrations as a result, for example, of manufacturing techniques and/or tolerances, are to be expected. Thus, example embodiments of the present invention should not be construed as limited to the particular shapes of regions illustrated herein but are to include deviations in shapes that result, for example, from manufacturing. For example, an implanted region illustrated as a rectangle will, typically, have rounded or curved features and/or a gradient of implant concentration at its edges rather than a binary change from implanted to non-implanted region. Likewise, a buried region formed by implantation may result in some implantation in the region between the buried region and the surface through which the implantation takes place. Thus, the regions illustrated in the figures are schematic in nature and their shapes are not intended to illustrate the actual shape of a region of a device and are not intended to limit the scope of the present invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Hereinafter, a photoalignment compound, an alignment composition, a display substrate, a method for manufacturing the display substrate will be sequentially described.

First, the photoalignment compound will be described.

The photoalignment compound is represented by, for example, the following Chemical Formula 1.

<Chemical Formula 1>

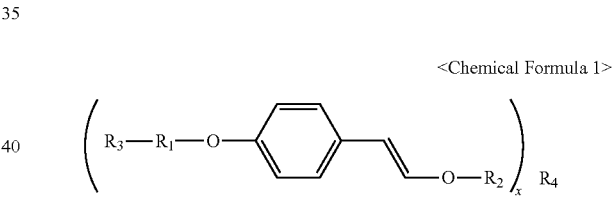

In Chemical Formula 1, "x" represents an integer in a range of 1 to 4, each of $R_1$ and $R_2$ represents —$(CH_2)_n$—, "n" represents an integer in a range of 1 to 6, at least one of the (—$CH_2$-)s in $R_1$ is replaceable with

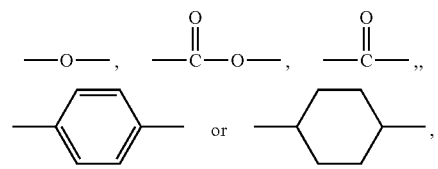

represents —$(CH_2)_m CH_3$, "m" represents an integer in a range of 1 to 12, each hydrogen atom of $R_3$ is replaceable with F or Cl, $R_4$ represents an amino group, aniline group, carboxy group, hydroxyl group, cyano group, alkyl group, or functional groups being represented by the following Chemical Formulas 2, 3, 4, or 5, each hydrogen atom of Chemical Formula 1 is replaceable with —$O(CH_2)_k CH_3$, —$(CH_2)_k CH_3$, F, or Cl, and "k" represents an integer in a range of 1 to 3, or 0.

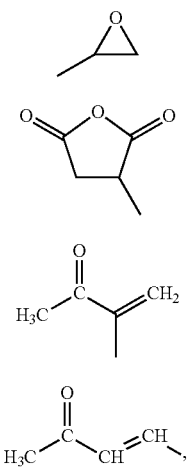

<Chemical Formula 2>

<Chemical Formula 3>

<Chemical Formula 4>

<Chemical Formula 5>

The specification has been amended as set forth above to correct a typographical error therein.

As a Comparative Example, a cinnamate photosensitive portion including an ester structure shown in the following Chemical Formula 10 is isomerized by light to be changed into a compound represented by the following Chemical Formula 11 including a heptagonal structure.

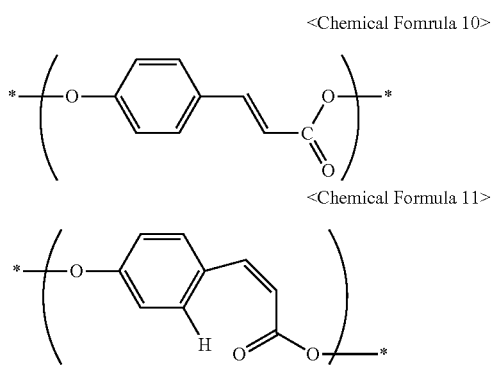

<Chemical Formula 10>

<Chemical Formula 11>

In an embodiment, the photosensitive portion may be represented by, for example, the following Chemical Formula 12.

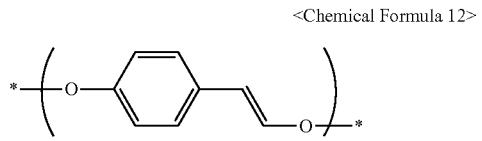

<Chemical Formula 12>

In Chemical Formula 12, each hydrogen atom may be replaceable with —O(CH$_2$)$_n$CH$_3$, —(CH$_2$)$_n$CH$_3$, F, or Cl. "n" represents an integer in a range of 1 to 3, or 0.

According to Chemical Formula 12, a double bond between carbon atoms may be combined with a functional group which stabilizes the double bond, and thus the photosensitive portion may be stabilized with the trans-type structure.

In addition, when the photosensitive portion represented by Chemical Formula 12 may be isomerized from the trans-type structure to the cis-type structure, the trans-type structure of the photosensitive portion may have a hexagonal structure (see the following Chemical Formula 8). The hexagonal structure is known to be chemically stable. In particular, the alignment stability of compounds including the cinnamate photosensitive portion and the photosensitive portion of the present invention will be described referring to FIGS. 1A and 1B.

Figure 1B:
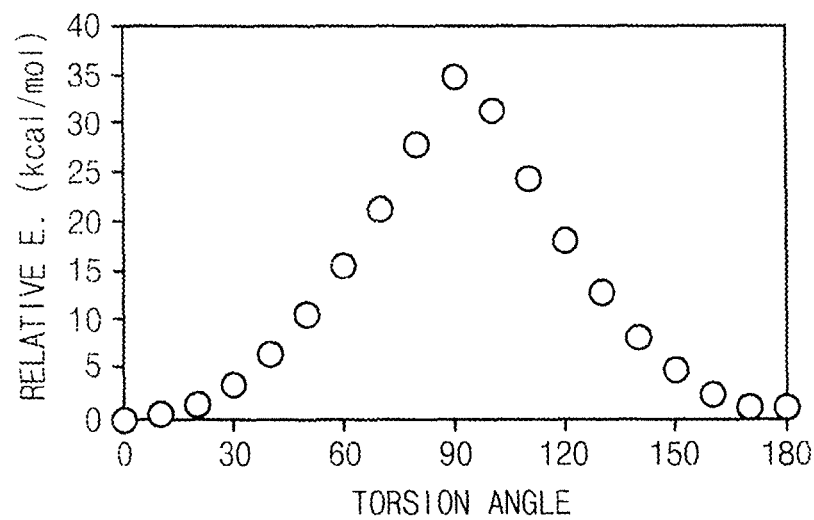
FIG. 1B is a graph illustrating relative energy according to a torsion angle of a compound according to an Example of the present invention.

FIG. 1A is a graph illustrating relative energy according to a torsion angle of a compound according to a Comparative Example. FIG. 1B is a graph illustrating relative energy according to a torsion angle of a compound according to an Example of the present invention.

The compound according to the Comparative Example was methyl cinnamate. The compound according to the Example of the present invention was (2-methoxy-vinyl)-benzene. The relative energy of each of methyl cinnamate and (2-methoxy-vinyl)-benzene according to a torsion angle was measured by using Jaguar version 5.5 (product name, Schrödinger, LLC, U.S.A.) as a simulation program, and thus the obtained results are illustrated in FIGS. 1A and 1B. In FIGS. 1A and 1B, when the torsion angle is "about 0°," the photosensitive portion has a cis-type structure, and when the torsion angle is "about 180°," the photosensitive portion has a trans-type structure.

Referring to FIG. 1A, when the torsion angle is about 0, the relative energy of the cis-type structure methyl cinnamate is about 4.7 kcal/mol. As the torsion angle in a range between about 0° to about 90° is increased, the relative energy may be increased. When the torsion angle is about 90°, the relative energy is about 35 kcal/mol. As the torsion angle in a range between about 90° to about 180° is increased, the relative energy may be decreased. When the torsion angle of the trans-type structure methyl cinnamate is about 180°, the relative energy is about 0 kcal/mol. In methyl cinnamate, the trans-type structure may be more stable than the cis-type structure.

Referring to FIG. 1B, when the torsion angle of the cis-type (2-methoxy-vinyl)-benzene is about 0°, the relative energy is about 0 kcal/mol. As the torsion angle in a range between about 0° to about 90° is increased, the relative energy may be increased. When the torsion angle of (2-methoxy-vinyl)-benzene is about 90°, the relative energy is about 35 kcal/mol. As the torsion angle in a range between about 90° to about 180° is increased, the relative energy may be decreased. When the torsion angle of (2-methoxy-vinyl)-benzene is about 180°, the relative energy is about 1.2 kcal/mol. Regarding (2-methoxy-vinyl)-benzene, the cis-type structure may be more stable than the trans-type structure.

When methyl cinnamate is irradiated by light, the trans-type structure is isomerized to be changed into the cis-type structure. However, the trans-type structure is less stable than the cis-type structure, because the energy of the cis-type structure is about 4.7 kcal/mol higher than that of the trans-type structure. Although the light is irradiated to the photosensitive portion, the cis-type structure may be readily isomerized to be changed into the trans-type structure having a stable state. Thus, a dimer of cinnamate may be hardly formed by polymerizing cinnamate photosensitive portions. Accordingly, when the photoalignment compound includes the cinnamate photosensitive portion, the alignment stability may be low thereby decreasing the reliability of the alignment layer.

In contrast, regarding (2-methoxy-vinyl)-benzene, the energy of the trans-type structure is about 1.2 kcal/mol higher than that of cis-type structure. The cis-type structure may be more stable than the trans-type structure. The isomerization of the photosensitive portion is relatively favored to the reverse isomerization. Thus, although the light is irradiated to the photosensitive portion, the reverse isomerization from the cis-type structure to the trans-type structure may be minimized.

According to an example of the present invention, an isomerization and/or dimerization may be favored by a photosensitive portion of a photoalignment compound, and, a reverse reaction of the isomerization and/or the dimerization may be prevented. Thus, the manufacturing reliability of an alignment layer, the alignment reliability of the alignment layer, and alignment stability may be improved.

In an example of the present invention, $R_3$ of Chemical Formula 1 may be a perpendicular manifestation portion, and $R_4$ of Chemical Formula 1 may be a polymerization portion. $R_1$ may be a spacer which connects the perpendicular manifestation portion to the polymerization portion. $R_2$ may be a spacer which connects the polymerization portion to the photosensitive portion.

Examples of the polymerization portion may include but are not limited to an amino group, carboxy group, hydroxyl group, cyano group, alkylene group, etc. For example, the polymerization portion may include two amino groups combined with at least one benzene ring. The polymerization portion may include, for example, a benzene ring of 1 to 5.

Particular examples of the polymerization may include but are not limited to para-phenylenediamine (p-PDA), 4,4'-methylenedianiline (MDA), 4,4'-oxydianiline (ODA), meta-bisaminophenoxydiphenylsulfone (m-BAPS), para-bisaminophenoxydiphenylsulfone (p-BAPS), 2,2-bisaminophenoxyphenylpropane (BAPP), 2,2-bisaminophenoxyphenylhexafluoropropane (HF-BAPP), 1,4-diamino-2-methoxybenzene, etc. These may be used alone or in a combination thereof.

One photoalignment compound may include a plurality of the photosensitive portions. For example, the photoalignment compound may include 1 to 4 of

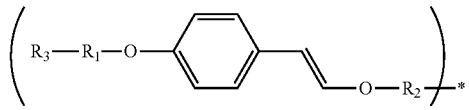

in Chemical Formula 1. 1 to 4 of

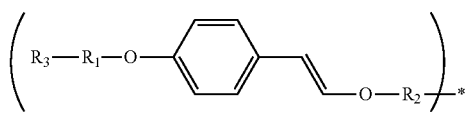

may be combined with $R_4$ as a side chain of $R_4$. For example, at least one hydrogen atom of $R_4$ may be replaced with

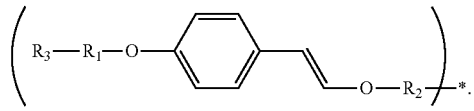

When the polymerization portion is phenyldiamine, 2 of 6 carbon atoms in a phenyl group of phenyldiamine may be combined with 2 amino groups, and the remaining 4 of the 6 carbon atoms may be combined with the photosensitive portions. When the polymerization portion is phenyldiamine, the photoalignment compound may include 1 to 4 of the photosensitive portions.

Particular examples of the photoalignment compound may include but are not limited to a compound represented by the following Chemical Formula 6. However, the present invention should not be construed as limited to the examples set forth herein.

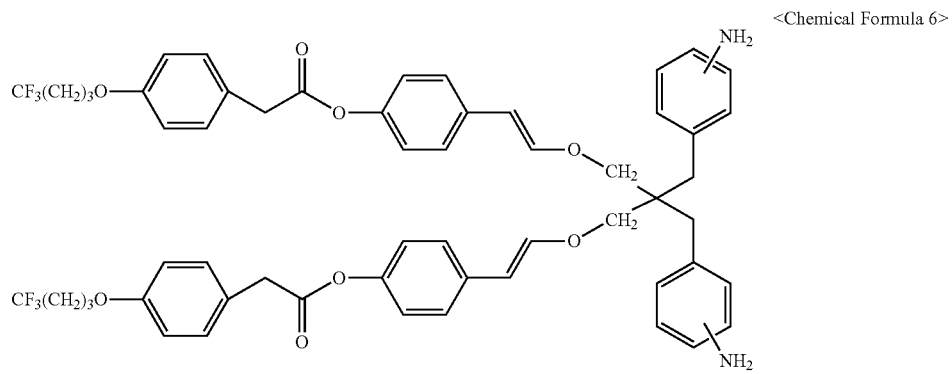

<Chemical Formula 6>

According to another embodiment of the present invention, $R_3$ of Chemical Formula 1 may be a perpendicular manifestation portion and $R_4$ of Chemical Formula 1 may be a thermal reaction portion. $R_1$ may be a spacer which is connected to the perpendicular manifestation portion and the thermal reaction. $R_1$ may be a spacer which connects the thermal reaction to the photosensitive portion. The photosensitive portion and the perpendicular manifestation portion is substantially the same as the photosensitive portion and the perpendicular manifestation that have been previously described. Thus, any repetitive description will be omitted.

The thermal reaction portion is combined with the photosensitive portion, and may react after the photoalignment compound is provided with heat. The thermal reaction portion may include, for example, a carbon-carbon bond and/or a carbon-oxygen bond which are readily broken by heat because the bond strength is weak. The photoalignment compound including the thermal reaction portion may be used for an additive of raw material used for forming an alignment layer and having a non-photosensitivity to form a photoalignment layer having a photosensitivity.

When heat is provided to a composite material including a polymer having non-photosensitivity and the photoalignment compound, the thermal reaction portion of the photoalignment compound may be chemically combined with the polymer by the heat. Thus, the photosensitive portion of the photoalignment compound may be inserted into the polymer to form a photoalignment polymer.

Examples of the thermal reaction portion may include compounds represented by the following Chemical Formulas 2, 3, 4, and 5. However, the present invention should not be construed as limited to the examples set forth herein.

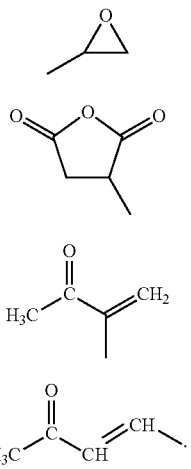

<Chemical Formula 2>

<Chemical Formula 3>

<Chemical Formula 4>

<Chemical Formula 5>

Hereinafter, a photoalignment composition of the present invention will be described.

The photoalignment composition includes a first alignment polymer that is a compound in which at least one hydrogen atom is replaced with a photosensitive portion, and an organic solvent.

The main chain may include a conventional polymer used in forming an alignment layer. An alignment direction of the alignment layer formed by using the conventional polymer may include a substantially perpendicular direction or a substantially parallel direction with respect to a surface of a substrate.

Particular examples of the main chain may include but are not limited to a polyimide compound, polyamic acid compound, polyamide compound, polynorbornene compound, polyvinyl compound, polyolefin compound, polystyrene compound, polyacrylate compound, polyether compound, polyester compound, polythioether compound, polysulfone compound, polyethersulfone compound, polyetherketone compound, polyurea compound, polyurethane compound, polybenzimidazole compound, polyacetal compound, polyvinyl acetate compound, polymaleimide compound, polyphenylene phthalamide compound, azo side-chain polymer compound, polycinnamoyl compound, polychalcone compound, polycoumarin compound, etc. These may be used alone or in a combination thereof.

The photosensitive portion may be represented by, for example, the following Chemical Formula 7.

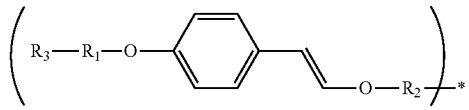

<Chemical Formula 7>

In Chemical Formula 7, each of R1 and R2 represents —(CH2)n-, "n" represents an integer in a range of 1 to 6, at least one of the (—CH2-)s in R1 is replaceable with

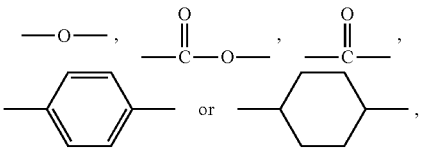

$R_3$ represents —(CH2)mCH3, "m" represents an integer in a range of 1 to 12, and each hydrogen atom of $R_3$ is replaceable with F or Cl.

$R_2$ of Chemical Formula 7 may be combined with the main chain.

Hereinafter, a method for forming the photoalignment compound represented by Chemical Formula 6 will be described.

First, about 1 mole of methyl 4-hydroxybenzoate and about 1 mole of 4-bromo-1,1,1-trifluorobutane were added to excess acetone which was mixed with potassium carbonate at a temperature of about 40° C. for about 90 minutes to obtain about 1 mole of methyl 4-(4,4,4-trifluorobutoxy)benzoate. About 1 mole of methyl 4-(4,4,4-trifluorobutoxy)benzoate was mixed with about 1 N (normality) of excess sodium hydroxide, and methyl 4-(4,4,4-trifluorobutoxy)benzoate and sodium hydroxide were mixed to perform reflux for about 30 minutes and then neutralized to hydrochloric acid to obtain about 1 mole of 4-(4,4,4-trifluorobutoxy)benzoic acid. About 1 mole of 4-(4,4,4-trifluorobutoxy)benzoic acid was mixed with carbon dichloride and carbonyl diimidazole (CDI). After 4-(4,4,4-trifluorobutoxy)benzoic acid, carbon dichloride, and CDI were reacted at a temperature of about 25° C. for about 2 hours. About 1 mole of 4-hydroxybenzaldehyde was mixed with the above mixture at a temperature of about 25° C. for about 12 hours and, carbon dichloride and water were added to extract about 1 mole of 4-formylphenyl 4-(4,4,4-trifluorobutoxy)benzoate.

About 2 mole of 1-bromomethyl)-4-nitrobenze and about 1 mole of dimethyl malonate were mixed with excess methyl ethyl ketone (MEK) which was mixed with potassium carbonate at a temperature of about 50° C. for about 3 hours. After adding excess water at temperature of about 25° C., the above materials were precipitated to obtain about 1 mole of dimethyl 2,2-bis(4-nitrobenzyl)malonate. About 1 mole of dimethyl 2,2-bis(4-nitrobenzyl)malonate was mixed with water and tetrahydrofurane (THF) which was mixed with lithium hydroxide, and dimethyl 2,2-bis(4-nitrobenzyl)malonate at a temperature of about 25° C. for about 22 hours. After adding about 1 N of hydrochloric acid at a temperature of about 25° C., excess water and ether were added to extract about 1 mole of 2,2-bis(4-nitrobenzyl)maloic acid. THF and borane were added to about 1 mole of 2,2-bis(4-nitrobenzyl) maloic acid and THF, borane at a temperature of about 25° C. for about 20 hours. After adding excess water and ethyl acetate, about 1 mole of 2,2-bis(4-nitrobenzyl)propane-1,3-diol was obtained. Formaldehyde was added to about 1 mole of 2,2-bis(4-nitrobenzyl)propane-1,3-diol, and 2,2-bis(4-nitrobenzyl)propane-1,3-diol at a temperature of about 80° C. for about 30 minutes. Hydrogen bromide was added to, and 2,2-bis(4-nitrobenzyl)propane-1,3-diol, formaldehyde, and hydrogen bromide were reacted at a temperature of about 25° C. for about 3 hours to obtain about 1 mole of 2,2-bis((bromomethoxy)methyl)-1,3-bis(4-nitrophenyl)propane. After adding triphenylphosphine and carbon dichloride to 2,2-bis((bromomethoxy)methyl)-1,3-bis(4-nitrophenyl)propane at a temperature of about 23° C. for about 2 hours, about 1 mole of 4-formylphenyl 4-(4,4,4-trifluorobutoxy)benzoate was mixed with excess sodium hydride and THF at a temperature of about 23° C. for about 18 hours. Then, zinc chloride and carbon dichloride are added at a temperature of about 40° C. for about 16 hours to obtain about 1 mole of the compound represented by Chemical Formula 6.

Hereinafter, a method for forming the first alignment polymer including polyamic acid and/or polyamide compound as a main chain will be described.

In an embodiment, the first alignment polymer may be formed by, for example, reacting a photoalignment compound and an anhydride.

The photoalignment compound is substantially the same as the previously described photoalignment compound including a photosensitive portion, a perpendicular manifestation portion, and a polymerization portion. Thus, any repetitive description will be omitted.

For example, $R_4$ of the photoalignment compound may be a phenyl diamine group. Methods traditionally known as copolymerizing polyamic acid and/or polyimide may be used in a method for copolymerizing the photoalignment compound and an anhydride to form a first alignment polymer including polyamic acid and/or polyimide.

In an embodiment, the first alignment polymer may be formed by, for example, combining the amino group (—$NH_2$) of a photoalignment compound and a ketone group (—CO—) of an anhydride to form an imide bond (—NH—CO—). For example, the first alignment polymer may include polyamic acid which is firstly formed by reacting the photoalignment compound and an anhydride, and polyimide which is formed by performing a dehydration and a ring closure reaction of polyamic acid. For example, the dehydration and the ring closure may be performed by heating polyamic acid, or reacting polyamic acid with the dehydrating agent or a catalyst for the dehydration and the ring closure.

Examples of an anhydride may include but are not limited to 1,2,3,4-cyclobutanetetracarboxylic acid dianhydride (CBDA), 5-(2,5-dioxotetrahydrofuryl)-3-methylcyclohexene-1,2-dicarboxylic dianhydride (DOCDA), bicyclooctene-2,3,5,6-tetracarboxylic dianhydride (BODA), 1,2,3,4-cyclopentanetetracarboxylic dianhydride (CPDA), 1,2,4,5-cyclohexanetetracarboxylic dianhydride (CHDA), 1,2,4-tricarboxy-3-methylcarboxycyclopentane dianhydride, 1,2,3,4-tetracarboxycyclopentane dianhydride, pyromellitic dianhydride (PMDA), biphthalic dianhydride (BPDA), oxydiphthalic dianhydride (ODPA), benzophenonetetracarboxylic dianhydride (BTDA), hexafluoroisopropylidenediphthalic dianhydride (6-FDA), etc. These may be used alone or in a combination thereof.

In an embodiment of the present invention, the first alignment polymer may be formed by, for example, reacting a photoalignment compound and a conventional alignment polymer.

The photoalignment compound is substantially the same as the previously described photoalignment compound including the thermal reaction portion, the photosensitive portion, and the perpendicular manifestation portion. In addition, the conventional alignment polymer is substantially the same as the main chain of the first alignment polymer previously described. Thus, any repetitive description will be omitted.

The conventional alignment polymer may include compounds which have non-photosensitivity and are used in rubbing alignment. The conventional alignment polymer may be aligned in a substantially perpendicular direction or a substantially parallel direction with respect to a surface of a substrate. In an embodiment of the present invention, the conventional alignment polymer may include a photosensitive portion different from the photosensitive portion disclosed above.

The first alignment polymer may be formed by, for example, heating the photoalignment compound and the conventional alignment polymer. When the thermal reaction portion of the photoalignment compound is heated, a carbon-carbon bond and/or a carbon-oxygen bond are broken, and then obtained products are combined with the conventional alignment polymer. Thus, the photosensitive portion may be formed at the conventional alignment polymer, and thus the first alignment polymer having photosensitivity may be formed.

The photoalignment composition may further include a second alignment polymer with the first alignment polymer.

The second alignment polymer may be added to the photoalignment composition independently with the first alignment polymer. The photoalignment composition may be a mixture mixed with the first alignment polymer and the second alignment polymer.

The second alignment polymer may include the conventional alignment polymer used in forming an alignment layer. The second alignment polymer may be used in rubbing alignment. The conventional alignment polymer may be aligned in a substantially perpendicular direction or a substantially parallel direction with respect to a surface of a substrate. Examples of the second alignment polymer may include but are not limited to a polyimide compound, polyamic acid compound, polyamide compound, polynorbornene compound, polyvinyl compound, polyolefin compound, polystyrene compound, polyacrylate compound, polyether compound, polyester compound, polythioether compound, polysulfone compound, polyethersulfone compound, polyetherketone compound, polyurea compound, polyurethane compound, polybenzimidazole compound, polyacetal compound, polyvinyl acetate compound, polymaleimide compound, polyphenylene phthalamide compound, azo side-chain polymer compound, polycinnamoyl compound, polychalcone compound, polycoumarin compound, etc. These may be used alone or in a combination thereof.

Examples of the organic solvent may include but are not limited to chlorobenzene, N-methylpyrrolidone, dimethyl sulfoxide, dimethylformamide, toluene, chloroform, gamma-butyrolactone, methyl cellosolve, butyl carbitol, tetrahydrofurane, etc. These may be used alone or in a combination thereof.

Hereinafter, a display substrate and a method for manufacturing the display substrate will be described.

Exemplary Embodiment 1

Figure 2:
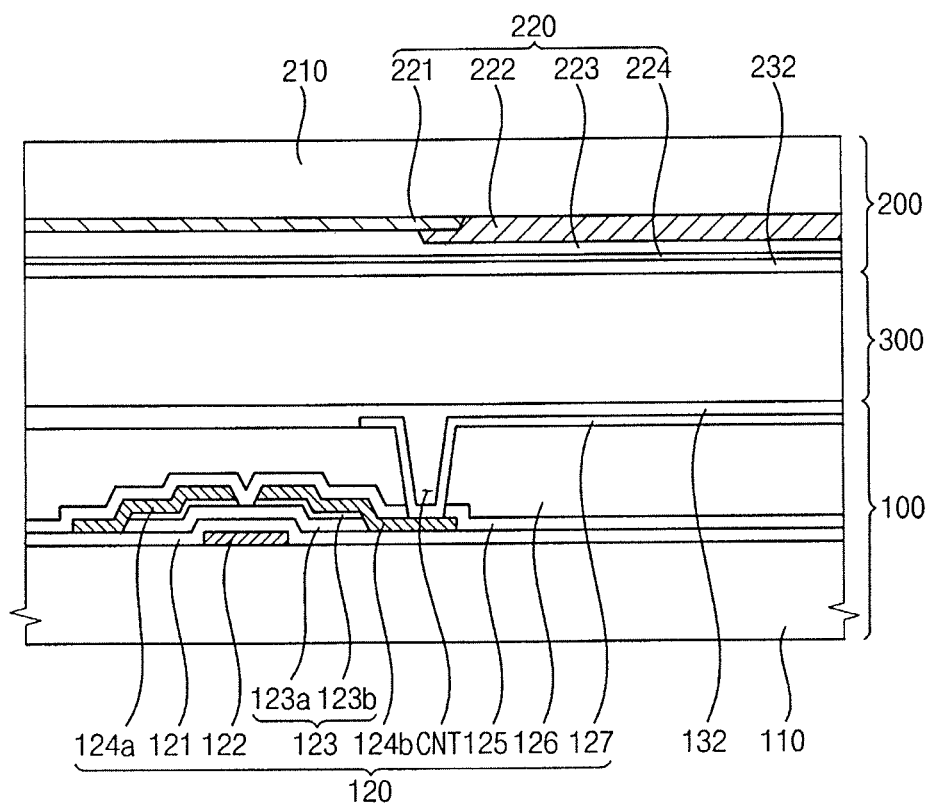
FIG. 2 is a cross-sectional view illustrating a display device according to an exemplary embodiment of the present invention.

FIG. 2 is a cross-sectional view illustrating a display device according to an exemplary embodiment of the present invention.

Referring to FIG. 2, a display device shown in FIG. 2 includes a first display substrate 100, a second display substrate 200, and a liquid crystal layer 300.

The first display substrate 100 includes a first base substrate 110, a first pixel layer 120 formed on the first base substrate 110, and a first alignment layer 132 formed on the first pixel layer 120.

The first pixel layer 120 includes a plurality of signal lines which divides a plurality of pixel units, a switching element formed on each of the pixel units, and a pixel electrode 127 electrically connected to the switching element and formed on each of the pixel units.

The signal lines include a plurality of gate lines and a plurality of data lines. The gate lines extend in a direction of the first base substrate 110. The data lines extend in a different direction to that of the gate lines. The pixel units may be divided by the gate and data lines.

Each of the switching elements may include a gate electrode 121, an active pattern 123, a source electrode 124a, and a drain electrode 124b.

The gate electrode 121 may be connected to the gate line.

The active pattern 123 is formed on the gate electrode 121 and under the source and drain electrodes 124a and 124b. The active pattern 123 is overlapped with the gate electrode 121. The active pattern 123 may include a semiconductor layer 123a and an ohmic contact layer 123b.

The source electrode 124a may be connected to the data line. The source electrode 124a may be overlapped with an edge portion of the active pattern 123. The drain electrode 124b may be spaced apart from the source electrode 124a. The drain electrode 124b may be overlapped with an opposite edge portion of the active pattern 123.

The pixel electrode 127 is formed on the switching element. The pixel electrode 127 contacts with the drain electrode 124b through a contact hole CNT. Thus, the pixel electrode 127 may be electrically connected to the switching element.

The first pixel layer 120 may further include a gate insulation layer 122, a passivation layer 125, and an organic layer 126.

The gate insulation layer 122 may be formed on the first base substrate 110 including the gate lines and the gate electrode 121. The passivation layer 125 may be formed on the first base substrate 110 including the data lines, the source electrode 124a, and the drain electrode 124b. The organic layer 126 may be formed on the first base substrate 110 including the passivation layer 125. The organic layer 126 may planarize the first display substrate 100. Forming the organic layer 126 may be omitted. The passivation layer 125 and the organic layer 126 may have the contact hole CNT exposing a portion of the drain electrode 124b.

The first alignment layer 132 includes a first alignment portion represented by, for example, the following Chemical Formula 8 and/or a second alignment portion represented by, for example, the following Chemical Formula 9.

<Chemical Formula 8>

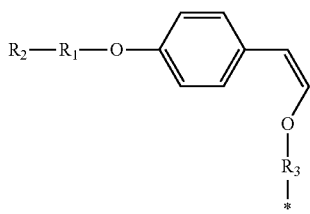

<Chemical Formula 9>

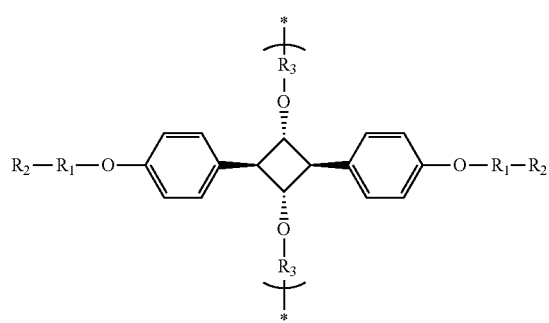

In Chemical Formulas 8 and 9, each of $R_1$ and $R_3$ represents —$(CH_2)_n$—, "n" represents an integer in a range of 1 to 6, at least one of the (—$CH_2$-)s in $R_1$ is replaceable with

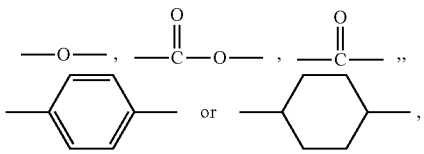

$R_2$ represents —$(CH_2)_m CH_3$, "m" represents an integer in a range of 1 to 12, and each hydrogen atom of $R_2$ is replaceable with F or Cl.

The first alignment layer 132 includes a photoalignment polymer including a main chain, in which at least one hydrogen atom is replaced with the first alignment portion and/or the second alignment portion.

Examples of the main chain may include but are not limited to a polyimide compound, polyamic acid compound, polyamide compound, polynorbornene compound, polyvinyl compound, polyolefin compound, polystyrene compound, polyacrylate compound, polyether compound, polyester compound, polythioether compound, polysulfone compound, polyethersulfone compound, polyetherketone compound, polyurea compound, polyurethane compound, polybenzimidazole compound, polyacetal compound, polyvinyl acetate compound, polymaleimide compound, polyphenylene phthalamide compound, azo side-chain polymer compound, polycinnamoyl compound, polychalcone compound, polycoumarin compound, etc. These may be used alone or in a combination thereof.

The first alignment portion has a hexagonal structure as a cis-type structure having carbon-carbon double bond. The hexagonal structure is known to be chemically stable. The first alignment portion as the cis-type structure may be more stable than the trans-type structure (refer to Chemical Formula 1) because the energy of the first alignment portion having the cis-type structure is lower than that of the trans-type structure of the first alignment portion by about 1.2 kcal/mol. The first alignment portion has the cis-type structure more stable than the trans-type structure, and thus the first alignment portion may be hardly isomerized to be changed into the trans-type structure of the first alignment portion, although external energy is provided to the first alignment portion. In addition, the second alignment portion is a dimer formed by, for example, polymerizing the first alignment portions, and the second alignment portion has a stable transition state. The second alignment portion has an ether structure more stable than ester. Thus, the alignment reliability and the stability of the first alignment layer 132 including the first and second photoalignment portions may be improved.

The second display substrate 200 includes a second pixel layer 220 formed on a second base substrate 210 opposite to the first display substrate 100, and a second alignment layer 232.

The second pixel layer 220 includes a black matrix pattern 221 which divides an area into a plurality of pixel units, a color filter 222 formed on each pixel unit, an overcoat layer 223, and a common electrode layer 224.

The black matrix pattern 221 may be formed on the second base substrate 210 corresponding to the gate lines, the data lines and the switching element.

The color filter 222 may be formed in each pixel unit divided by the black matrix pattern 221. The black matrix pattern 221 may be disposed between color filters 222 adjacent to each other.

The overcoat layer 223 is formed on the second base substrate 210 including the black matrix pattern 221 and the color filter 222. The overcoat layer 223 may planarize the second display substrate 200. The overcoat layer 223 may be omitted.

The common electrode layer 223 may be formed on the second base substrate 210 including the overcoat layer 223. When the overcoat layer 223 is omitted, the common electrode layer 224 may be directly formed on the black matrix pattern 221 and the color filter 223 to make contact with the black matrix pattern 221 and the color filter 223.

The second alignment layer 232 may be formed on the second base substrate 210 including the common electrode layer 224. Liquid crystal molecules of the liquid crystal layer 300 may be disposed between the second alignment layer 232 and the first alignment layer 132. The second alignment layer 232 is substantially the same as the first alignment layer 132, except that the second alignment layer 232 is formed on the second base substrate 210. Thus, any repetitive description will be omitted.

The liquid crystal layer 300 is interposed between the first display substrate 100 and the second display substrate 200. The liquid crystal molecules of the liquid crystal layer 300 may be stably disposed between the first and second alignment layers 132 and 232.

Figure 3A:
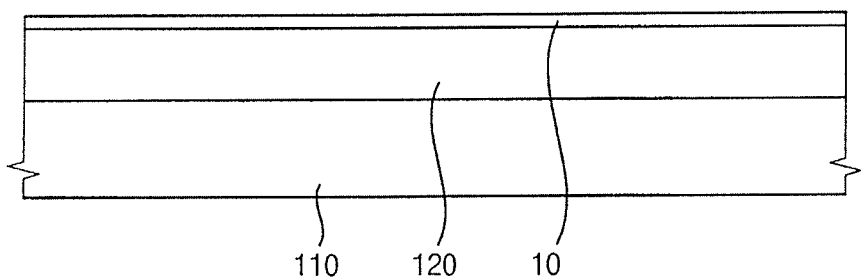
FIGS. 3A and 3B are cross-sectional views illustrating a method for manufacturing the first display substrate shown in FIG. 2.
Figure 3B:
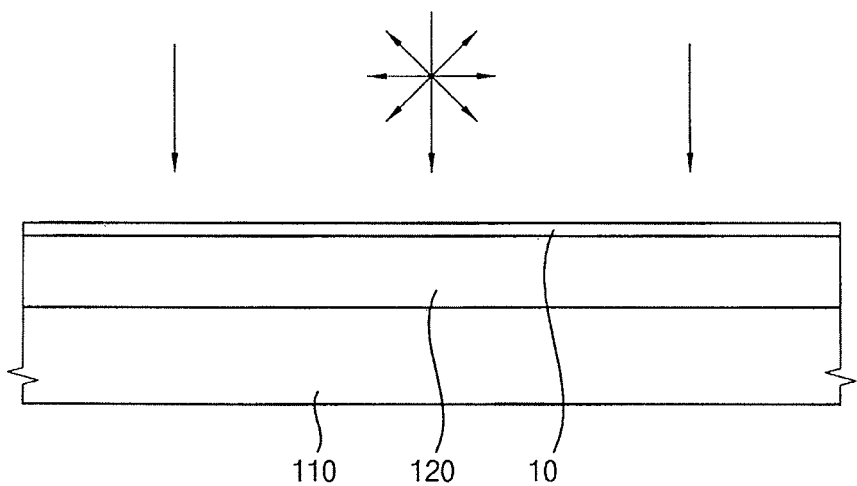

FIGS. 3A and 3B are cross-sectional views illustrating a method for manufacturing a first display substrate shown in FIG. 2.

Referring to FIG. 3A, the first pixel layer 120 is formed on the first base substrate 110. Forming the first pixel layer 120 will be described with reference to FIG. 2.

Referring to FIG. 2, the gate lines and the gate electrode 121 are formed on the first base substrate 110. For example, a gate metal layer may be formed on the first base substrate 110, and the gate metal layer may be patterned by a photolithography process to form the gate lines and the gate electrode 121.

The gate insulation layer 122 is formed on the first base substrate 110 including the gate lines and the gate electrode 121. Examples of a material that may be used for the gate insulation layer 122 may include but are not limited to silicon oxide, silicon nitride, etc.

The semiconductor layer 123a and the ohmic contact layer 123b are formed on the first base substrate 110 including the gate insulation layer 122. For example, the semiconductor layer 123a may be formed using amorphous silicon, the ohmic contact layer 123b may be formed using amorphous silicon into which $n^+$ impurities are implanted at a high concentration. The semiconductor layer 123a and the ohmic contact layer 123b are patterned by, for example, a photolithography process to form the active pattern 123.

The data lines, the source electrode 124a and the drain electrode 124b are formed on the first base substrate 110 including the active pattern 123. For example, a source metal layer may be formed on the first base substrate 110 including the active pattern 123, and the source metal layer may be patterned by a photolithography process to form the data lines, the source electrode 124a and the drain electrode 124b.

The passivation layer 125 and the organic layer 126 may be formed on the first base substrate 110 including the data lines, the source electrode 124a and the drain electrode 124b. The passivation layer 125 may be formed using, for example, silicon oxide, silicon nitride, etc. The organic layer 126 may be formed using, for example, a positive-type photoresist composition.

A portion of the passivation layer 125 and the organic layer 126 corresponding to the drain electrode 124b may be removed to form the contact hole CNT exposing a portion of the drain electrode 124b.

A transparent electrode layer is formed on the first base substrate 110 including the passivation layer 125 and the organic layer 126 which include the contact hole CNT. The transparent electrode layer may be patterned by, for example, a photolithography process to form the pixel electrode 127. Examples of a material that may be used for the transparent electrode layer may include but are not limited to indium tin oxide, indium zinc oxide, etc.

Referring again to FIG. 3A, a first preliminary layer 10 is formed on the first base substrate 110 including the pixel electrode 127.

The first preliminary layer 10 may be formed by, for example, coating a photoalignment composition including a first alignment polymer on the first base substrate 110 including the pixel electrode 127. The first preliminary layer 10 may be formed by, for example, a chemical vapor deposition (CVD). In an embodiment of the present invention, the first preliminary layer 10 may be formed by, for example, rolling, jetting or spin-coating the photoalignment composition.

The first alignment polymer includes, for example, a photosensitive portion represented by the following Chemical Formula 7 and a main chain, in which at least one hydrogen atom is replaced with the photosensitive portion.

<Chemical Formula 7>

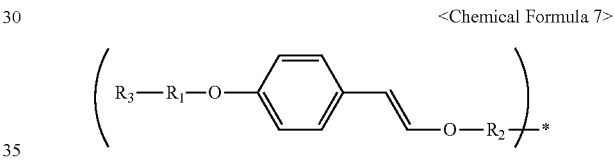

Chemical Formula 7, each of R1 and R2 represents —(CH2)n-, "n" represents an integer in a range of 1 to 6, at least one of the (—CH2-)s in R1 is replaceable with

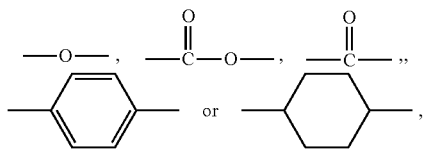

R3 represents —(CH2)mCH3, "m" represents an integer in a range of 1 to 12, and each hydrogen atom of R3 is replaceable with F or Cl.

Examples of the main chain may include but are not limited to a polyimide compound, polyamic acid compound, polyamide compound, polynorbornene compound, polyvinyl compound, polyolefin compound, polystyrene compound, polyacrylate compound, polyether compound, polyester compound, polythioether compound, polysulfone compound, polyethersulfone compound, polyetherketone compound, polyurea compound, polyurethane compound, polybenzimidazole compound, polyacetal compound, polyvinyl acetate compound, polymaleimide compound, polyphenylene phthalamide compound, azo side-chain polymer compound, polycinnamoyl compound, polychalcone compound, polycoumarin compound, etc. These may be used alone or in a combination thereof.

Referring to FIG. 3B, polarized light is irradiated to the first base substrate 110 including the first preliminary layer 10.

For example, the polarized light may be ultraviolet light. The polarized light may provide a carbon-carbon double bond of the photosensitive portion represented by Chemical Formula 7 with energy.

The photosensitive portion of the trans-type structure represented by Chemical Formula 7 may be isomerized to be the cis-type structure represented by Chemical Formula 8.

<Chemical Formula 8>

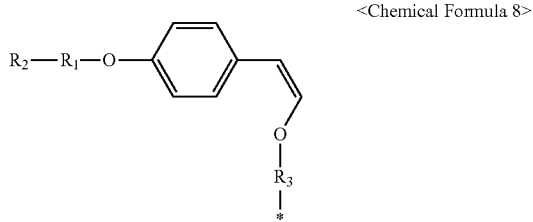

In Chemical Formula 8, each of $R_1$ and $R_3$ represents —$(CH_2)_n$—, "n" represents an integer in a range of 1 to 6, at least one of the (—$CH_2$-)s in $R_1$ is replaceable with

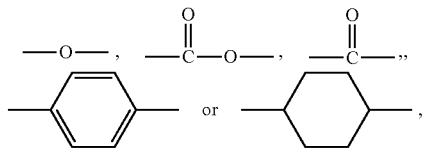

$R_2$ represents —$(CH_2)_m CH_3$, "m" represents an integer in a range of 1 to 12, and each hydrogen atom of $R_2$ is replaceable with F or Cl.

In addition, the second photoalignment portion may be formed by, for example, the dimerization between the first photoalignment portions adjacent to each other.

<Chemical Formula 9>

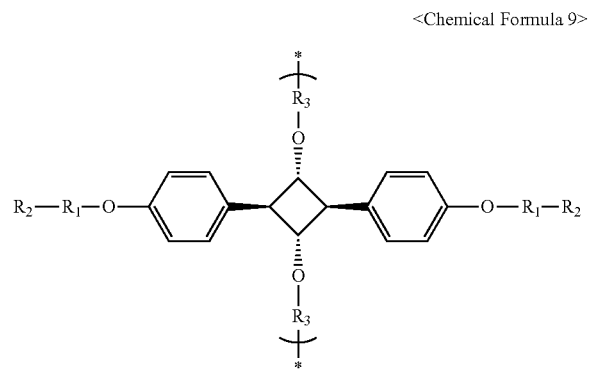

In Chemical Formula 9, each of $R_1$ and $R_3$ represents —$(CH_2)_n$—, "n" represents an integer in a range of 1 to 6, at least one of the (—$CH_2$-)s in $R_1$ is replaceable with

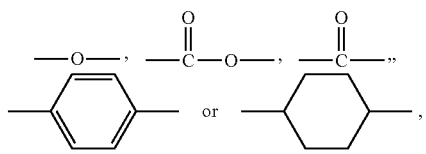

$R_2$ represents —$(CH_2)_m CH_3$, "m" represents an integer in a range of 1 to 12, and each hydrogen atom of $R_2$ is replaceable with F or Cl.

By providing the preliminary layer 10 with the polarized light, the first alignment polymer may be, for example, isomerized and/or dimerized to form the first alignment layer 132 including the photoalignment polymer. Thus, the first display substrate shown in FIG. 1 may be manufactured.

In addition, a surface of the first alignment layer 132 may have a pretilt angle by, for example, irradiating an ion beam to the first alignment layer 132. The first and/or second photoalignment portions on a surface of the first alignment layer 132 may be slanted with respect to the first base substrate 110 by the ion beam to have the pretilt angle.

Hereinafter, a method for manufacturing the second display substrate will be described referring to FIG. 2.

In the method for manufacturing the second display substrate shown in FIG. 2, the method is substantially the same as the method for manufacturing the first display substrate shown in FIG. 2, except for forming the second pixel layer 220. In addition, the forming of the second alignment layer is substantially the same as forming the first alignment layer except that the second alignment layer is formed on the second display substrate. Thus, any repetitive description will be omitted.

Referring to FIG. 2, first, the second pixel layer 220 is formed on the second base substrate 210, to manufacture the second display substrate 200.

The black matrix pattern 221 is formed on the second base substrate 210. For example, the black matrix pattern 221 may be formed by forming a metal layer including chromium (Cr) and patterning the metal layer using a photolithography process. In an embodiment of the present invention, the black matrix pattern 221 may be formed by, for example, jetting an organic ink.

The color filter 222 is formed on the second base substrate 222 including the black matrix pattern 221. For example, a color photoresist layer may be formed on the second base substrate 210, and the color photoresist layer may be patterned by a photolithography process to form the color filter 222. In an embodiment of the present invention, the color filter 222 may be formed by, for example, jetting a color ink.

The overcoat layer 223 is formed on the second base substrate including the black matrix pattern 221 and the color filter 222. For example, the overcoat layer 224 may be formed using an acrylic resin.

The common electrode layer 224 is formed on the second base substrate 210 including the overcoat layer 223. For example, the common electrode layer 224 may be formed by forming a transparent electrode layer and patterning the transparent electrode layer using a photolithography process.

The second alignment layer 232 is formed on the second base substrate 210 including the common electrode layer 224. For example, the first alignment polymer is coated on the common electrode layer 224, the polarized light is irradiated to the first alignment polymer to form the photoalignment polymer, and then the second alignment layer 232 is formed. Thus, the second display substrate 220 shown in FIG. 2 including the second alignment layer 232 is manufactured.

Exemplary Embodiment 2

A display device according to Exemplary Embodiment 2 is substantially the same as the display device shown in FIG. 2. Thus, any repetitive description will be omitted.

In addition, manufacturing methods for a first display substrate and a second display substrate of the display device are substantially the same as the manufacturing methods for the first and second display substrates shown in FIG. 1, except for forming a first alignment layer and forming a second alignment layer. Thus, any repetitive description will be omitted.

Hereinafter, a method for manufacturing the first display substrate will be described referring to FIGS. 4A and 4B.

Figure 4A:
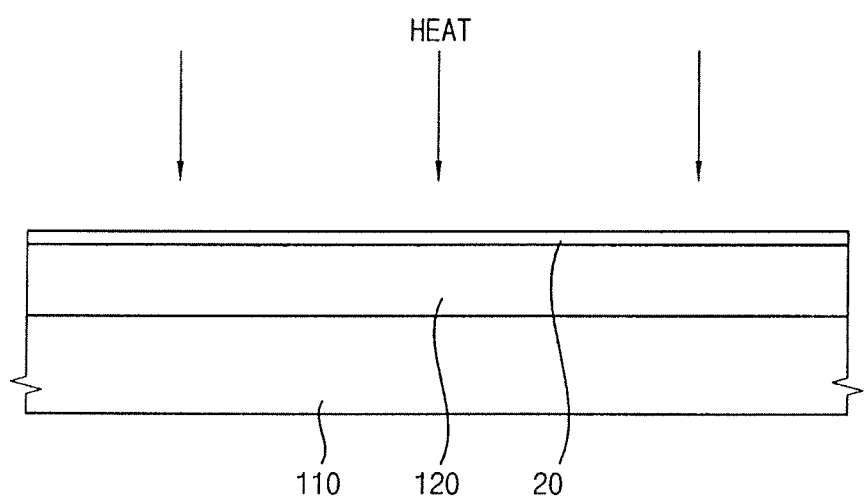
FIGS. 4A and 4B are cross-sectional views illustrating a method for manufacturing a first display substrate according to an exemplary embodiment of the present invention.
Figure 4B:
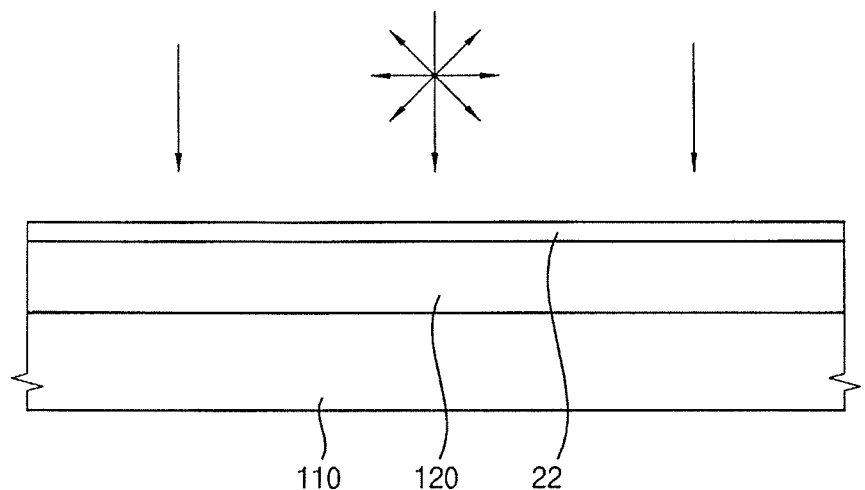

FIGS. 4A and 4B are cross-sectional views illustrating a method for manufacturing a first display substrate according to Embodiment 2 of the present invention.

Referring to FIG. 4A, a first composite material layer 20 is formed on a first base substrate 110 including a first pixel layer 120.

The first composite material layer 20 includes, for example, a conventional alignment polymer, a photoalignment compound represented by the following Chemical Formula 1, and an organic solvent.

<Chemical Formula 1>

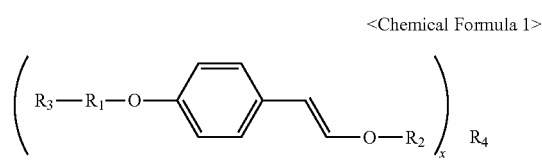

"x" represents an integer in a range of 1 to 4, each of $R_1$ and $R_2$ represents "n" represents an integer in a range of 1 to 6, at least one of the (—$CH_2$-)s in $R_1$ is replaceable with

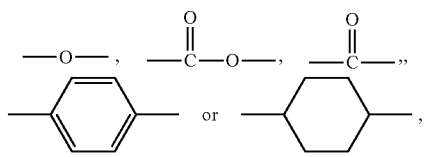

$R_3$ represents —$(CH_2)_m CH_3$, "m" represents an integer in a range of 1 to 12, each hydrogen atom of $R_3$ is replaceable with F or Cl, $R_4$ represents functional groups being represented by the following Chemical Formulas 2, 3, 4, or 5, each hydrogen atom of Chemical Formula 1 is replaceable with —$O(CH_2)_k CH_3$, —$(CH_2)_k CH_3$, F, or Cl, and "k" represents an integer in a range of 1 to 3, or 0.

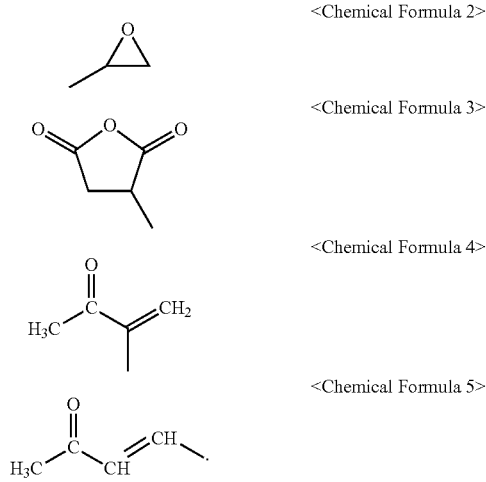

<Chemical Formula 2>

<Chemical Formula 3>

<Chemical Formula 4>

<Chemical Formula 5>

The conventional alignment polymer may include a photosensitive portion different form the photosensitive portion represented by Chemical Formula 1 or have non-photosensitivity. Examples of the conventional alignment polymer may include but are not limited to a polyimide compound, polyamic acid compound, polyamide compound, polynorbornene compound, polyvinyl compound, polyolefin compound, polystyrene compound, polyacrylate compound, polyether compound, polyester compound, polythioether compound, polysulfone compound, polyethersulfone compound, polyetherketone compound, polyurea compound, polyurethane compound, polybenzimidazole compound, polyacetal compound, polyvinyl acetate compound, polymaleimide compound, polyphenylene phthalamide compound, azo side-chain polymer compound, polycinnamoyl compound, polychalcone compound, polycoumarin compound, etc. These may be used alone or in a combination thereof.

Examples of the organic solvent may include but are not limited to chlorobenzene, N-methylpyrrolidone, dimethylsulfoxide, dimethylformamide, toluene, chloroform, gamma-butyrolactone, methyl cellosolve, butyl carbitol, tetrahydrofurane, etc. These may be used alone or in a combination thereof.

The first composite material layer 20 may be formed by coating a photoalignment composition including the conventional polymer and the photoalignment compound using CVD process on the first base substrate 110. In an embodiment of the present invention, the first composite material layer 20 may be formed by, for example, rolling, jetting or spin-coating the photoalignment composition.

The first base substrate 110 including the first composite material layer 20 is heated. After the first composite material layer 20 is heated, the conventional polymer and the photoalignment compound may be combined with each other. The thermal reaction portion of the photoalignment compound is broken to be combined with the conventional polymer as a side chain.

For example, the thermal treatment may include a pre-baking process and a hard-baking process. First, the photoalignment composition is coated on the first base substrate 110 including the first pixel electrode 120. The first base substrate 110 including the first pixel electrode 120 and the photoalignment composition is pre-baked to vaporize the organic solvent. The pre-baking process may be performed at, for example, a temperature of about 50° C. to about 70° C.

The photoalignment composition which is pre-baked may be hard-baked. The hard-baking process may be performed at, for example, a temperature of about 180° C. to about 220° C. Through the hard-baking process, the thermal reaction portion of the photoalignment compound may be broken to be chemically combined with the conventional alignment polymer.

Referring to FIG. 4B, by chemically combining the conventional alignment polymer and the photoalignment compound, a second preliminary layer 22 including a first alignment polymer is formed on the first pixel layer 120.

The polarized light may be irradiated to the second preliminary layer 22 to form the first alignment layer 132. The forming of the first alignment layer 132 by irradiating the polarized light to the first alignment polymer of the second preliminary layer 22 is substantially the same as forming the first alignment layer shown in FIGS. 3A and 3B. Thus, any repetitive description will be omitted.

Thus, the first display substrate according to Embodiment 2 is manufactured.

Also, a method for manufacturing the second display substrate is substantially the same as the method for the second display substrate according to Embodiment 1, except for forming the second alignment layer. The forming of the second alignment layer is substantially the same as forming the first alignment layer previously described. Thus, any repetitive description will be omitted.

Exemplary Embodiment 3

Figure 5:
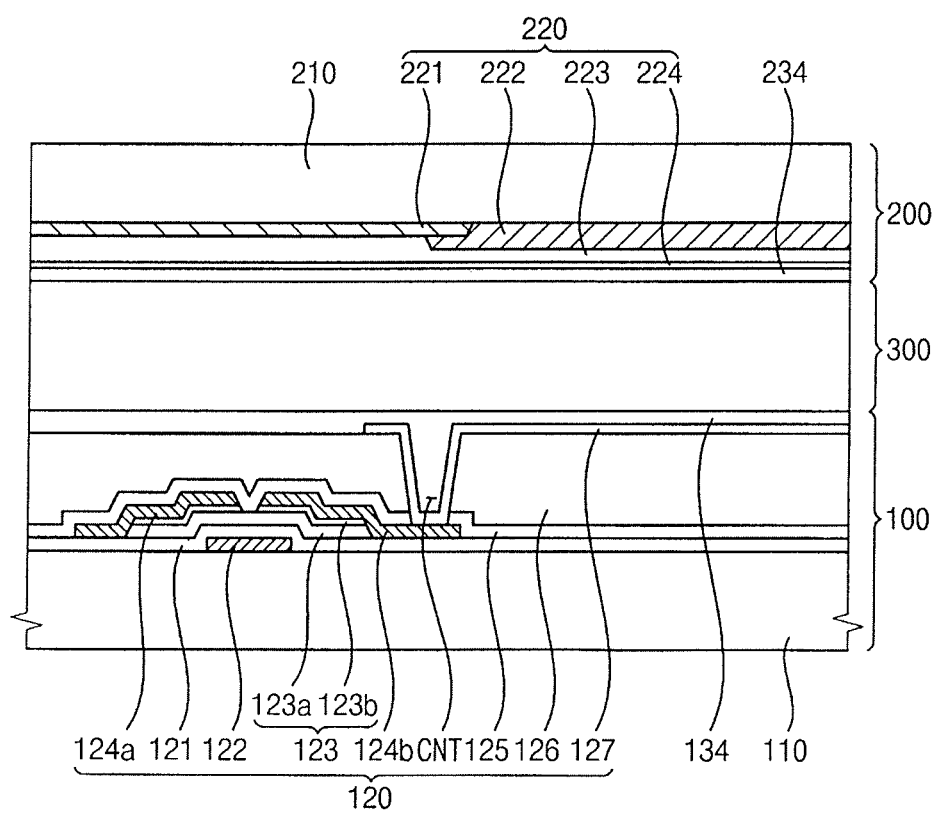
FIG. 5 is a cross-sectional view illustrating a display device according to an exemplary embodiment of the present invention.

FIG. 5 is a cross-sectional view illustrating a display device according to Exemplary Embodiment 3 of the present invention.

A display device shown in FIG. 5 is substantially the same as the display device shown in FIG. 2, except for a first alignment layer and a second alignment layer. Thus, any repetitive description will be omitted.

Referring to FIG. 5, a first display substrate 100 includes a first base substrate 100, a first pixel layer 120 formed on the first base substrate 110, and a first alignment layer 134 formed on the first pixel layer 120.

The first alignment layer 134 includes a first photoalignment portion represented by, for example, the following Chemical Formula 8, and/or a second photoalignment portion represented by, for example, the following Chemical Formula 9, and a main chain, in which at least one hydrogen atom is replaced with the first and/or second photoalignment portions.

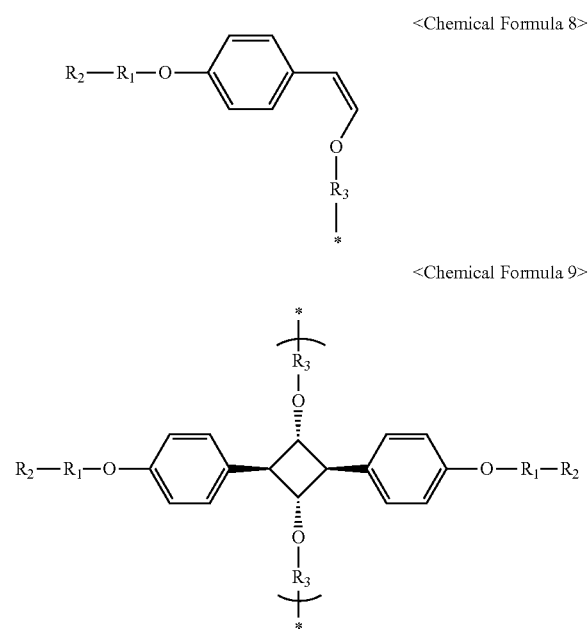

In Chemical Formulas 8 and 9, each of $R_1$ and $R_3$ represents —$(CH_2)_n$—, "n" represents an integer in a range of 1 to 6, at least one of the (—$CH_2$-)s in $R_1$ is replaceable with

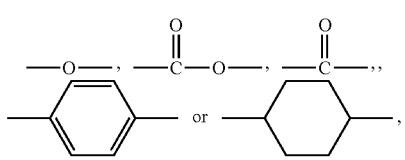

$R_2$ represents —$(CH_2)_m CH_3$, "m" represents an integer in a range of 1 to 12, and each hydrogen atom of $R_2$ is replaceable with F or Cl.

Examples of the main chain may include but are not limited to a polyimide compound, polyamic acid compound, polyamide compound, polynorbornene compound, polyvinyl compound, polyolefin compound, polystyrene compound, polyacrylate compound, polyether compound, polyester compound, polythioether compound, polysulfone compound, polyethersulfone compound, polyetherketone compound, polyurea compound, polyurethane compound, polybenzimidazole compound, polyacetal compound, polyvinyl acetate compound, polymaleimide compound, polyphenylene phthalamide compound, azo side-chain polymer compound, polycinnamoyl compound, polychalcone compound, polycoumarin compound, etc. These may be used alone or in a combination thereof.

The first alignment layer 134 may further include a second alignment polymer. The second alignment polymer includes a conventional alignment polymer. Examples of the second alignment polymer may include but are not limited to a polyimide compound, polyamic acid compound, polyamide compound, polynorbornene compound, polyvinyl compound, polyolefin compound, polystyrene compound, polyacrylate compound, polyether compound, polyester compound, polythioether compound, polysulfone compound, polyethersulfone compound, polyetherketone compound, polyurea compound, polyurethane compound, polybenzimidazole compound, polyacetal compound, polyvinyl acetate compound, polymaleimide compound, polyphenylene phthalamide compound, azo side-chain polymer compound, polycinnamoyl compound, polychalcone compound, polycoumarin compound, etc. These may be used alone or in a combination thereof.

The first alignment layer 134 may be formed by, for example, mixing the photoalignment polymer and the second alignment polymer. The second alignment polymer may be twisted with the main chain to be mixed with the main chain. The second alignment polymer may serve as a wall in which alignment polymer may support the first and/or second photoalignment portions stably to be disposed on a surface of the first alignment layer 134.

The second display substrate 200 shown in FIG. 5 includes a second pixel layer 220 formed on a second base substrate 210 and a second alignment layer 234 formed on the second pixel layer 220. The second alignment layer 234 is substantially the same as the first alignment layer 234. Thus, any repetitive description will be omitted.

Hereinafter, a method for manufacturing the first display substrate shown in FIG. 5 will be described referring to FIG. 6. The method is substantially the same as the method described in FIG. 2, except for forming the first alignment layer. Thus, any repetitive description will be omitted.

Figure 6:
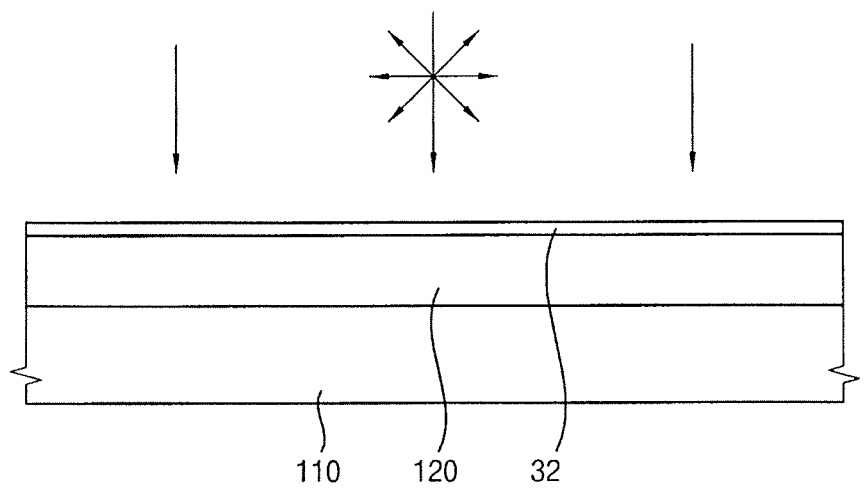
FIG. 6 is a cross-sectional view illustrating a method for manufacturing the first display substrate shown in FIG. 5.

FIG. 6 is a cross-sectional view illustrating a method for manufacturing the first display substrate shown in FIG. 5.

Referring to FIG. 6, the first pixel layer 120 is formed on the first base substrate 110. A third preliminary layer 32 is formed on the first pixel layer 120.

The third preliminary layer 32 includes a first alignment polymer and a second alignment polymer. The third preliminary layer 32 may be formed by, for example, simply mixing the first and second alignment polymers.

The first alignment polymer includes a photosensitive portion represented by, for example, the following Chemical Formula 7 and a main chain combined with the photosensitive portion.

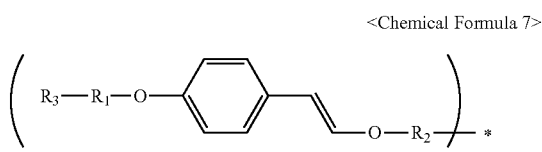

<Chemical Formula 7>

In Chemical Formula 7, each of $R_1$ and $R_2$ represents $—(CH_2)_n—$, "n" represents an integer in a range of 1 to 6, at least one of the ($—CH_2-$)s in $R_1$ is replaceable with

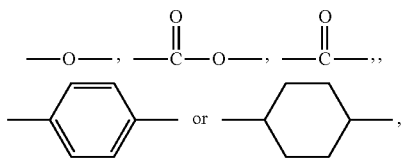

$R_3$ represents $—(CH_2)_mCH_3$, "m" represents an integer in a range of 1 to 12, and each hydrogen atom of $R_3$ is replaceable with F or Cl.

The second alignment polymer includes a conventional alignment polymer.

The polarized light is irradiated to the first base substrate 110 including the third preliminary layer 32 to form the first alignment layer 134.

By the polarized light, the photosensitive portion of the first alignment polymer is isomerized to be the first alignment portion represented by, for example, the following Chemical Formula 8 or dimerized to be the second alignment portion represented by, for example, the following Chemical Formula 9.

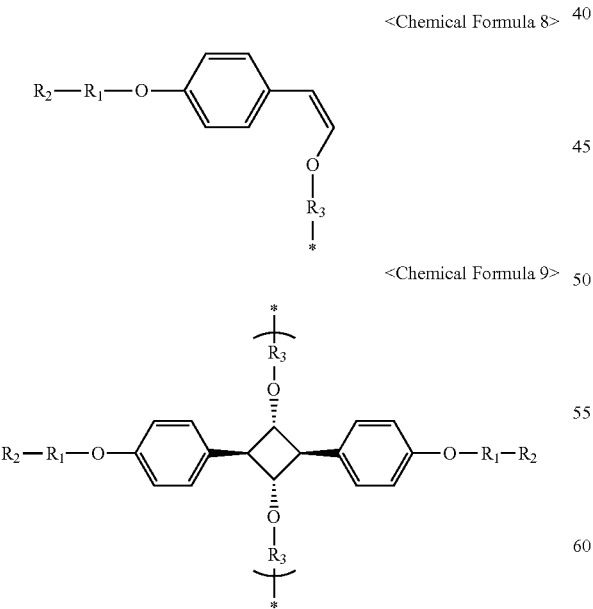

<Chemical Formula 8>

<Chemical Formula 9>

In Chemical Formulas 8 and 9, each of $R_1$ and $R_3$ represents $—(CH_2)_n—$, "n" represents an integer in a range of 1 to 6, at least one of the ($—CH_2-$)s in $R_1$ is replaceable with

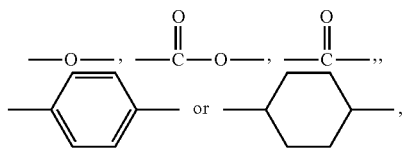

$R_2$ represents $—(CH_2)_mCH_3$, "m" represents an integer in a range of 1 to 12, and each hydrogen atom of $R_2$ is replaceable with F or Cl. Thus, the first display substrate according to Embodiment 3 is manufactured.

In a method for manufacturing the second display substrate according to Embodiment 3, forming the second alignment layer 234 is substantially the same as forming the first alignment layer 134. Thus, any repetitive description will be omitted.

According to exemplary embodiments of the present invention, an isomerization and/or dimerization may be favored by a photosensitive portion of a photoalignment compound. A cis-type structure of the photoalignment compound may be more stable than a trans-type structure of the photoalignment compound. Thus, the photoalignment compound including the photosensitive portion may be directly used in forming a photoalignment polymer including the photosensitive portion. In addition, the photoalignment compound may be used in an additive which is added to a conventional alignment polymer to form a photoalignment polymer.

By using the photoalignment compound of exemplary embodiments of the present invention, the manufacturing reliability of an alignment layer, the alignment reliability of the alignment layer, and alignment stability may be improved. In addition, the photosensitive portion of the photoalignment compound may be inserted into a conventional alignment material having non-photosensitivity, and thus development costs of a new photoalignment polymer may be decreased. Thus, the productivity of the product may be improved.

Having described the exemplary embodiments of the present invention, it is further noted that it is readily apparent to those of reasonable skill in the art that various modifications may be made without departing from the spirit and scope of the invention which is defined by the metes and bounds of the appended claims.

The invention claimed is:

1. A photoalignment compound represented by the following Chemical Formula 1,

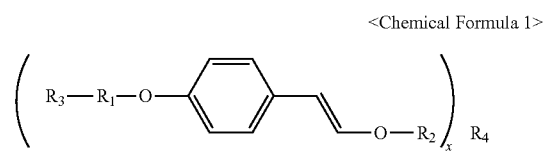

<Chemical Formula 1> wherein "x" represents an integer in a range of 1 to 4, each of $R_1$ and $R_2$ represents $—(CH_2)_n—$, "n" represents an integer in a range of 1 to 6, at least one of the ($—CH_2-$)s in $R_1$ is replaceable with

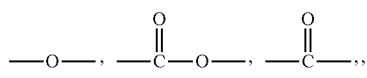

-continued

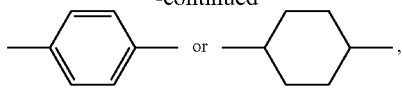

$R_3$ represents —$(CH_2)_mCH_3$, "m" represents an integer in a range of 1 to 12, each hydrogen atom of $R_3$ is replaceable with F or Cl, each hydrogen atom of Chemical Formula 1 is replaceable with —$O(CH_2)_kCH_3$, —$(CH_2)_kCH_3$, F, or Cl, and "k" represents an integer in a range of 1 to 3, or 0, and wherein $R_4$ represents an aminophenyl alkylbenzene amine.

2. A photoalignment compound represented by the following Chemical Formula 6,

<Chemical Formula 6>

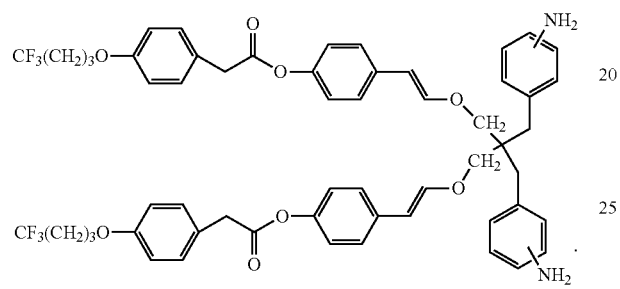

* * * * *